US007806916B2

(12) United States Patent
Delaloye et al.

(10) Patent No.: US 7,806,916 B2
(45) Date of Patent: Oct. 5, 2010

(54) APPLICATION SYSTEM FOR A STENT

(75) Inventors: Stéphane Delaloye, Bülach (CH); Karsten Koop, Rostock (DE); Dragica Pantic, Zürich (DE); Barbara Rast, Oberwenigen (CH)

(73) Assignee: Biotronik VI Patent AG, Baar (CH)

( * ) Notice: Subject to any disclaimer, the term of this patent is extended or adjusted under 35 U.S.C. 154(b) by 166 days.

(21) Appl. No.: 11/558,276

(22) Filed: Nov. 9, 2006

(65) Prior Publication Data

US 2007/0106366 A1 May 10, 2007

(30) Foreign Application Priority Data

Nov. 9, 2005 (DE) ...................... 10 2005 053 393

(51) Int. Cl.
*A61F 2/06* (2006.01)

(52) U.S. Cl. .................................................... 623/1.11

(58) Field of Classification Search ................ 623/1.11, 623/1.12
See application file for complete search history.

(56) References Cited

U.S. PATENT DOCUMENTS

| | | | | |
|---|---|---|---|---|
| 5,776,141 | A | 7/1998 | Klein et al. | |
| 5,935,135 | A | 8/1999 | Bramfitt et al. | |
| 6,494,906 | B1 * | 12/2002 | Owens | 623/1.11 |
| 6,818,013 | B2 * | 11/2004 | Mitelberg et al. | 623/1.15 |
| 2002/0120322 | A1 * | 8/2002 | Thompson et al. | 623/1.11 |
| 2003/0033001 | A1 * | 2/2003 | Igaki | 623/1.11 |
| 2003/0074044 | A1 | 4/2003 | Randby et al. | |

FOREIGN PATENT DOCUMENTS

| | | |
|---|---|---|
| EP | 0 282 175 | 9/1988 |
| WO | WO 95/31945 | 11/1995 |
| WO | WO 02/054986 | 11/2001 |
| WO | WO 2004/091446 | 4/2004 |
| WO | WO 2004/103217 | 4/2004 |
| WO | WO 2005/055879 | 12/2004 |
| WO | WO 2006/026201 | 8/2005 |

* cited by examiner

*Primary Examiner*—Bruce E Snow
(74) *Attorney, Agent, or Firm*—Jason A. Bernstein; Barnes & Thornburg LLP

(57) ABSTRACT

An application system for a stent comprising a catheter having at least one retention structure permanently connected to the catheter and a stent drawn onto the catheter using at least one retention element. The retention structure provides a retention area which receives and fixes the retention element. The retention element of the stent and the retention structure of the catheter have their geometry and position tailored to one another in such a way that the retention element is located in the retention area of the retention structure in the non-expanded state of the stent and the retention structure and/or the retention element are offset to one another upon expansion of the stent or at least in the expanded state of the stent so that the retention element is no longer located in the retention area of the retention structure.

20 Claims, 2 Drawing Sheets

10
17 13 14 16 12

20
17 22 14
23
17 24 14

A-A

APPLICATION SYSTEM FOR A STENT

PRIORITY CLAIM

This patent application claims priority to German Patent Application No. DE 10 2005 053 393.0, filed Nov. 9, 2005, the disclosure of which is incorporated herein by reference in its entirety.

FIELD OF THE INVENTION

The present invention relates to an application system for a stent.

BACKGROUND OF THE INVENTION

Stents are used to a continuously increasing extent in modern implantation technology for stabilizing/supporting hollow organs. The approach appears particularly suitable for coronary cardiac illnesses such as acute myocardial infarctions, which represent one of the most frequent causes of death in Western Europe and America. In more than 80% of the cases, the cause of the myocardial infarction is the thrombotic closure of a coronary artery through rupture of an atheromatous plaque upon pre-existing stenotic atheromatosis. Decisive factors for the long-term prognosis after acute myocardial infarction are (i) effective and long-standing reopening of the infrarcted artery, (ii) a duration of the thrombotic vessel closure, (iii) preventing greater myocardial loss and ventricular remodeling, and (iv) managing of rhythmogenic complications. The cited factors determine not only the cardiovascular mortality, but rather also the quality of life after the infarction.

For more than 20 years, nonoperative methods for stenosis treatment have been established, in which the constricted or closed blood vessel is expanded again, inter alia, by balloon dilation (PTA, percutaneous transluminal angioplasty). This procedure has proven itself in particular in the treatment of acute myocardial infarction. To prevent renewed closure of the expanded vessel by obstruction, a stent is used.

An application system is necessary for introducing and precisely placing the stent—referred to in the following in summary as application. The system comprises two components: the implant itself and a catheter, using which the application of the stent may be performed. Both components must be tailored to one another to perform the application of the stent as reliably as possible and with minimum operative effort.

On the part of the stent, a structure is to be provided which supports the implantation procedure and, in addition, ensures that the desired functionality may be observed at the implantation location. This is achieved, inter alia, in that the tubular stent is designed as expandable; upon application, the stent is first brought in a non-expanded state to the implantation location and transferred there using suitable means to an expanded state. The expansion may be caused by application of a mechanical force, e.g., inflation of a balloon, or may result from a structure itself, if memory materials are used in the stent, for example.

On the part of the catheter, adaptations are required, inter alia, as a function of the stent type used: one differs between self-expanding stents and balloon-expandable stents. For the first stent type, means must be provided which induce the self-expansion of the stent. The latter stent type makes the use of a balloon catheter necessary, and the stent is expanded at the implantation location by inflation of the balloon.

A partial problem in optimizing application systems for stents of this type is preventing slipping or even loss of the stent during the transport to the implantation location and during the implantation. One approach provides coating the stent supported on the catheter using a protective film which entirely or partially covers the stent. The film is typically to be composed so that the film either tears upon expansion of the stent or may be elastically stretched together with the stent. The approach will unavoidably result in parts or the entire film remaining in the body and a mechanical resistance of the film influencing the expansion behavior of the stent. Furthermore, a circumference of the application system is enlarged.

SUMMARY OF THE INVENTION

A feature of the present invention is to provide an improved, or at least alternative, application system for a stent, which offers protection from loss or displacement of the stent on the catheter during the transport to the implantation location and during the implantation.

According to the present invention, the application system comprises, in one embodiment, a catheter having at least one retention structure permanently connected to the catheter and a stent drawn onto the catheter using at least one retention element. The retention structure provides a retention area, which is implemented to receive and fix the retention element. The retention element of the stent and the retention structure of the catheter have their geometry and position tailored to one another in such a way that (i) the retention element is located in the retention area of the retention structure in the non-expanded state of the stent; and (ii) the retention structure and/or the retention element are offset to one another upon expansion of the stent or at least in the expanded state of the stent in such way that the retention element is no longer located in the retention area of the retention structure.

With the aid of the application system according to the present invention, it is possible to provide the stent with a hold on the catheter, without the structures interfering during application or the structures remaining entirely or partially in the body of the patient. The application system according to the present invention increases the friction retention force of the stent on the catheter by the fixing in the axial direction and prevents undesired opening of the stent in curvy vessels by fixing the stent in the radial direction.

The catheter used according to the present invention is accordingly distinguished in that the catheter has a retention structure which is permanently connected thereto, e.g., through gluing or welding, or through one-piece implementation together with a further component of the catheter, such as the balloon or the catheter shaft. Such a catheter is not known in the prior art and is thus a further feature of the present invention.

A retention area of the retention structure is implemented according to the present invention to receive and fix the retention element. This means that the retention area is to have its geometry and also the properties of the components of the retention structure necessary for implementing this retention area adapted to the retention element of the stent. Geometrical adaptation in this definition requires that the retention area is at least to be predefined in its dimensions in such a way that the retention area may receive the retention element. If the components for defining the retention area are movable, in particular through the use of elastomer materials, this is to be taken into consideration in the design of the retention structure. A specific retention structure will be worked out by those skilled in the art with little effort using knowledge of the complementary retention element. Those skilled in the art may also orient themselves from the examples below.

The retention element of the stent and the retention structure of the catheter are especially adapted to one another in geometry and position according to the present invention. In the non-expanded state, the retention element of the stent is located in the retention area of the retention structure and may be fixed there supported by clamping and friction forces, for example. In this way, it is ensured that the stent does not shift on the catheter or even get lost during the guiding of the catheter to the implantation location. At the implantation location, the stent is expanded. The expansion of the stent contains an aspect essential for the present invention: the structural elements of the stent are partially deformed during the expansion. This, in turn, requires that a starting position of a specific structural element in relation to further structural elements of the stent may deviate from a relative position of this structural element after expansion. In other words, a movement of individual structural elements occurs in the peripheral surface (which enlarges upon expansion) of the stent. Structural elements which move in the peripheral surface of the stent in this definition are suitable as retention elements for the purposes according to the present invention. Those skilled in the art will either be able to detect the dimensions of the movement of the structural elements upon the expansion of the stent through models or ascertain the dimensions of the movement of the structural elements through simple expansion experiments. Structural elements having a relatively large movement upon expansion are especially suitable for the purposes according to the present invention.

With knowledge of the movement of the structural element selected as a retention element, those skilled in the art will have to design the complementary retention structure on the catheter. The receiving area of the retention structure is to be predefined in such a way that the retention structure and/or the retention element are offset to one another, upon expansion of the stent or at least in the expanded state of the stent, to an extent that the retention element is no longer located in the retention area of the retention structure. In other words, the stent is no longer fixed by the retention structure of the catheter. Those skilled in the art will be able to establish the required adaptations in shape and position of the particular complementary element on the basis of this simple consideration either starting from the retention structure of the catheter or starting from the retention element of the stent. Those skilled in the art may also orient themselves further from the examples below.

A stent suitable for the purposes of the present invention has at least one retention element of the type described above. The stent typically has a base frame made of support struts, whose relative orientation and dimensioning are variable to a high degree. The base frame of the stent preferably comprises a metallic material, since the movement of individual structural elements required for the purposes according to the present invention is executed in a more defined way if a material of this type is predefined than with, for example, polymer materials, and the implementation of the fixing according to the present invention is thus made easier. The material is especially preferably a magnesium alloy, which is possibly also biodegradable, or a material having a comparable modulus of elasticity.

The application system may comprise multiple retention structures and retention elements. The catheter preferably has 3 to 10 retention structures, 3 to 5 retention structures preferably being situated uniformly around the circumference of the catheter. The stent has a number of retention elements corresponding to the number of retention structures of the catheter. The retention structures on the catheter may extend over the entire length of the area which receives the stent, or may only be provided in the area of the stent ends.

According to a preferred embodiment, the catheter is a balloon catheter and, accordingly, the stent is balloon-expandable. Precisely the interaction between the balloon and the movement of the structural elements of the stent on the balloon, explained in greater detail above, suggests itself for the application system according to the present invention.

In an exemplary embodiment preferred for catheters and particularly balloon catheters, the retention structure is a band which is connected at each of its two ends via one connection point to the catheter. The connection between the band and the catheter at the connection points may be produced through welding or gluing, for example. The band may preferably be tensioned over the balloon of the balloon catheter or one end of the band may be attached in the section of the balloon which receives the stent and the other end may be attached outside this area on the catheter. A retention area of the retention structure in the meaning of the present invention extends between the catheter surface and the bottom side of the band. The complementary retention element on the stent is pushed under the band in the non-expanded state of the stent.

According to a preferred embodiment of the above-mentioned exemplary embodiment variations, the band comprises a thermoplastic elastomer. This has the advantage that the elasticity of the material is usable to increase the retention force, i.e., the retention element is pushed under a tensioned band and the retention force is increased by the resulting tension force. Furthermore, the material has the advantage that tearing of the band during the expansion of the stent may be avoided and, upon the subsequent deflation of the balloon, the retention structure is largely returnable to its starting position.

In the above-mentioned exemplary embodiments, the band and the catheter in the area of the connection point preferably comprise the same material. In this way, an especially simple, but also reliable, connection of the retention structure may be produced, e.g., through welding methods or gluing; since the material properties of the two components to be connected are identical, tearing of the retention structure upon mechanical strain is avoided.

The retention structure may have an outer edge in the retention area. This outer edge is preferably at an angle of less than 45°, particularly less than 20°, especially preferably less than 10° to the longitudinal axis of the catheter. Using the cited predefined angles, it is ensured that the retention structure does not catch in the body of the patient during insertion and removal of the catheter.

Furthermore, the retention element of the stent is preferably implemented in the form of an open tab, which is preferably situated on the stent end. An open tab in the meaning of the present invention is understood to mean a retention element which comprises a web element, which is connected at one end to the further structural elements of the stent, but is free at its other end from any further connection to the stent structure. This web element which forms the open tab may be oriented around the circumference, but possibly also in the longitudinal direction or an angle lying between them, depending on how the associated, complementary retention structure of the catheter is implemented and/or situated. Web elements for open tabs whose free ends point around the circumference are preferred. Stents having a retention element in the above-mentioned meaning are not known from the prior art and are, therefore, a further feature of the present invention.

In a further exemplary embodiment of the application system, the stent has a strut which has at least one section having a zigzag or wavy course in the crimped state, the section is used as a retention element, and the section is implemented so that the section is offset in relation to the retention structure of the catheter upon expansion of the stent. With such a retention element, the geometrically required opening of the structure in the course of the expansion of the stent is used for the release from the retention structure of the catheter. The section which is used as a retention element is preferably part of an annular peripheral strut of the stent, which is preferably situated on the stent end of the stent. Structures of this type may be manufactured especially easily.

The present invention is explained in greater detail in the following on the basis of exemplary embodiments in the associated drawings.

DESCRIPTION OF THE INVENTION

Figure 1:
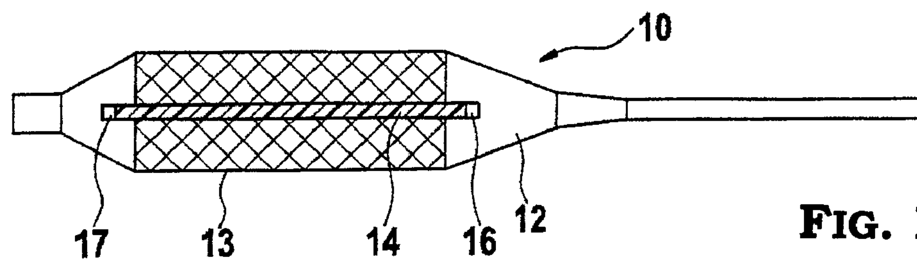
FIG. 1 shows the distal end of a balloon catheter having a retention structure according to one exemplary embodiment of the present invention.

FIG. 1 is a simplified illustration of the distal end of a balloon catheter 10 having a dilatable balloon 12, on which a stent 13, which is only indicated schematically for the purpose of clarity, is drawn by crimping. The balloon 12 is typically molded from a thermoplastic polymer. According to the variation shown in FIG. 1, a retention structure is provided, which is implemented as a band 14, whose two ends are each bound via connection points 16 and 17 to the catheter 10. The connection points 16 and 17 are selected according to the present example so that the band 14 extends over the entire length of the balloon 12 and the band 14 runs largely parallel to a longitudinal axis of the catheter 10. The band 14 comprises a thermoplastic polymer, particularly a polyurethane, as is also used for the components of the catheter 10 in the area of the connection points 16 and 17. For the purpose of simplified illustration of the principle according to the present invention, only a single band 14 is shown in FIG. 1. However, the catheter preferably has 3 to 5 bands of this type, which are situated spaced uniformly around the circumference of the catheter.

Figure 2A:
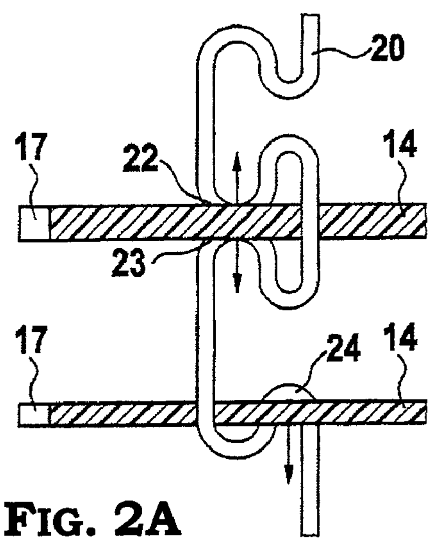
FIG. 2A shows an enlarged detail from an uncoiled stent, as is usable for a retention structure according to FIG. 1, in the area of the retention element according to the present invention and in interaction with a retention structure of the catheter according to the present invention in the non-expanded state.
Figure 2B:
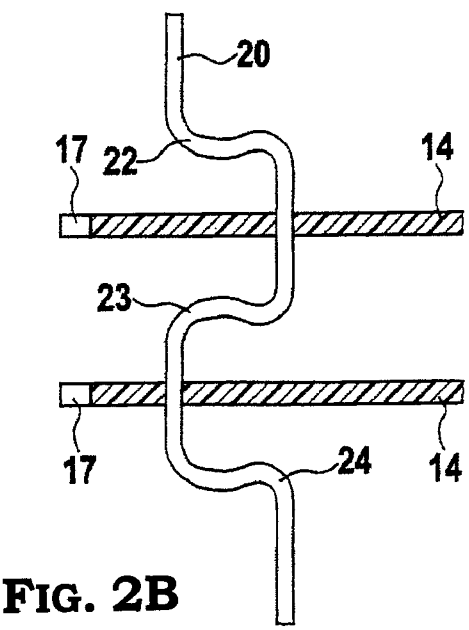
FIG. 2B shows an enlarged detail from an uncoiled stent, as is usable for a retention structure according to FIG. 1, in the area of the retention element according to the present invention and in interaction with a retention structure of the catheter according to the present invention in the expanded state.

FIGS. 2A and 2B show enlarged details of an application system having a retention structure on the catheter from FIG. 1. The figures show a detail from an uncoiled stent 13, once in the non-expanded state of the stent 13 (FIG. 2A) and, in addition, in the expanded state of the stent 13 (FIG. 2B). The detail shown contains a strut 20, which continues annularly around the circumference. The part of the strut 20 shown is preferably situated on the stent end; illustration of the structural elements of the stent adjoining this annular peripheral strut having been dispensed with for reasons of clarity.

In the detail shown in FIG. 2A, the strut 20 has a total of 3 sections 22, 23, 24, which act as retention elements in the meaning of the present invention. The sections 22 and 23 are each implemented as arcs, whose two tips press against one another in the non-expanded state of the stent 13 or are at least so close to one another that a gap resulting between them has dimensions smaller than the width of the band 14. The curved section 24 defines a further retention element, which may be provided for the purposes of the present invention in the area of the stent 13. As shown, the band 14 spans the sections 22, 23, 24 of the strut 20. If the stent structure is now expanded by inflating the balloon 12, the strut 20 experiences stretching and/or the individual sections 22, 23, 24 move in relation to the band 14. The movement occurs in such a way that the sections 22, 23, 24 under the band 14 are pulled out (indicated by the arrows in FIG. 2A). As a result, the stent 13 is no longer fixed via the band 14 and associated retention element on the stent (see FIG. 2B).

Figure 3A:
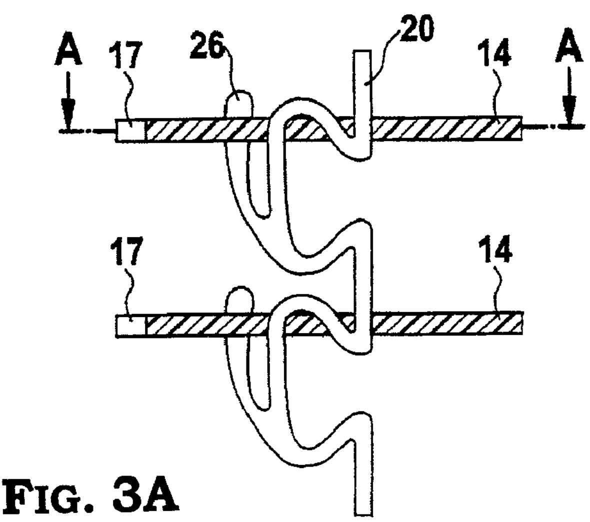
FIG. 3A shows a retention element on the stent in the form of open tabs and in interaction with a retention structure of the catheter in the non-expanded state of the stent.
Figure 3B:
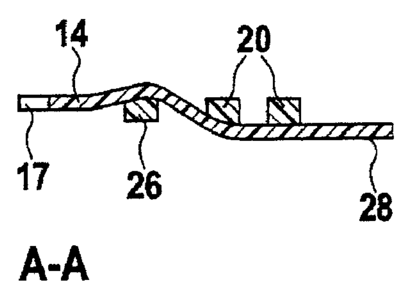
FIG. 3B shows a cut-away view taken along line A-A of FIG. 3A.

FIGS. 3A-B shows a further exemplary embodiment of the retention element on the stent 13 with an otherwise identical exemplary embodiment of the retention structure according to the preceding figure; also again restricted in illustration to a detail of the unwinding of the stent. A peripheral strut 20 displays a structure whose shaping may be referred to as an open tab on its distal end. The open tab is formed by an arm 26 placed on the strut 20 which points around the circumference. FIGS. 3A-B also shows a section along line A-A, which illustrates the position of the band 14 in the non-expanded state of the stent 13. Upon expansion of the stent by balloon inflation, because of the predefined structure, the arm 26 is retracted far enough that the arm is no longer under the band 14 (the movement is not shown here).

Figure 4:
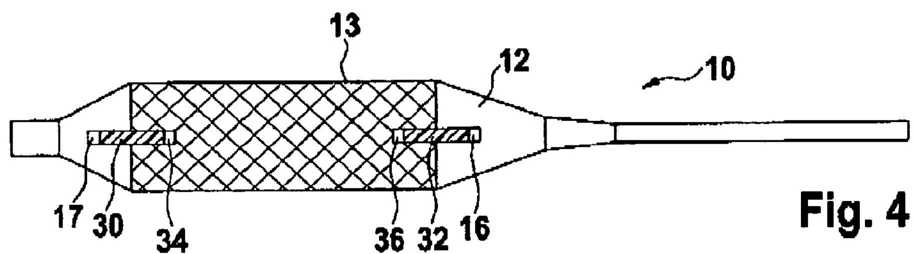
FIG. 4 shows the distal end of a balloon catheter having a further, band-like exemplary embodiment of the retention structure according to the present invention.
Figure 5A:
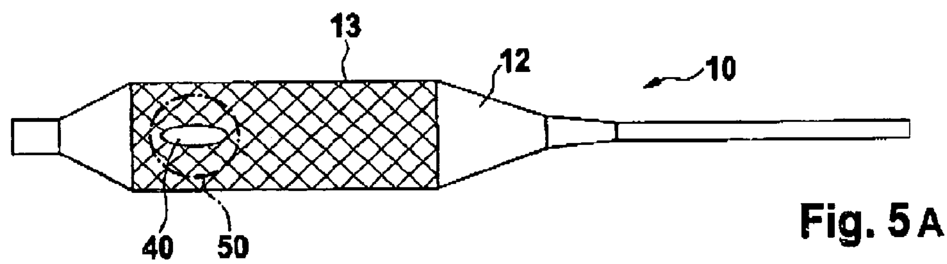
FIG. 5A shows the distal end of a balloon catheter having a further exemplary embodiment of the retention structure according to the present invention.
Figure 5B:
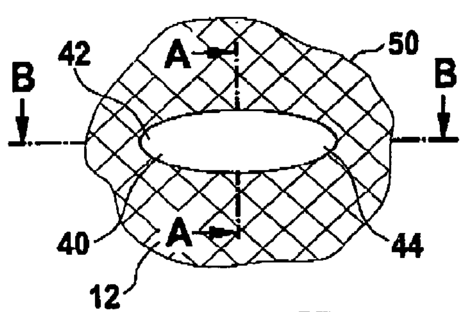
FIG. 5B shows an enlarged view of a portion of the retention structure of FIG. 5A.
Figure 5C:
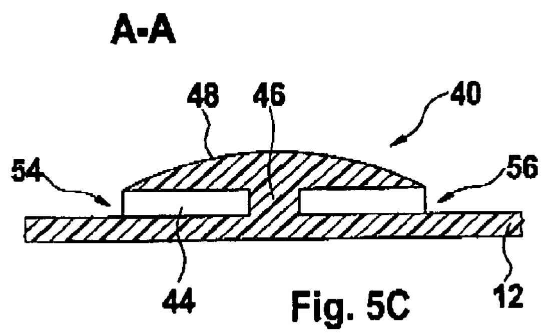
FIG. 5C is a cut-away view taken along line A-A of FIG. 5B.
Figure 5D:
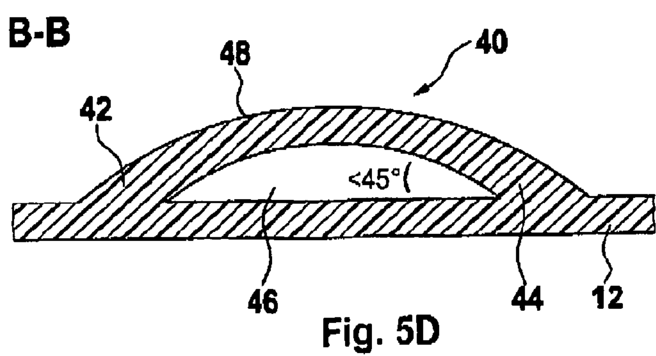
FIG. 5D is a cut-away view taken along line B-B of FIG. 5B.

FIG. 4 shows a variation of the application largely based on FIG. 1. The exemplary embodiment differs only in that a band 14 which spans the entire balloon 12 is not provided, but rather only two short bands 30, 32, whose ends 34 and 36, respectively, are attached in the area of the balloon 12 which carries the stent 13 or are fixed directly on the balloon 12 by the stent 13.

FIGS. 5A-D schematically shows a further exemplary embodiment of the application system having a retention element 40 permanently connected at the distal end of the catheter 10. The circular detail 50 is enlarged and shown in two sections along lines A-A and B-B. The retention element 40 has an oblong contour and is oriented parallel to the longitudinal direction of the catheter 10. As may be seen from the sections along lines A-A (FIG. 5C) and B-B (FIG. 5D), the retention structure 40 is connected permanently to the balloon 12 at its distal and proximal ends and centrally along a middle strut 46. The retention structure 40 has a cap 48 rounded outward, which has two undercuts 54, 56 approximately centrally. The undercuts 54, 56 correspond to the retention area of the retention structure 40.

Retention elements of the stent for a retention structure 40 according to FIGS. 5A-D are to be predefined in such a way that the retention elements may engage in the undercuts 52, 54 of the retention element 40 because of their dimensions (particularly their width) and are fixed there, possibly supported by clamping force. Upon expansion of the stent, the structure of the stent is to be predefined so that the retention elements may be pulled out of the retention structure 40 again.

The invention claimed is:

1. An application system for a stent, comprising:

a) a catheter having at least one retention structure, each retention structure having an elongated portion having a top surface, a bottom surface, a first end and a second end, and having generally parallel opposing first and second sides, the first and second ends being fixedly attached to the catheter, a portion of the retention structure not being attached to the catheter; and b) a stent drawn onto the catheter using at least one retention element, the retention element having arcuate or curved sections, wherein each retention structure provides a retention area defined by at least two distinct generally coplanar and opposing points of contact with bottom surface of the retention element and between the connections to the catheter and which receives and fixes the retention element, and the retention element of the stent and the retention structure of the catheter have their geometry and position tailored to one another so that:

(i) the retention element is located in the retention area of the retention structure in the non-expanded state of the stent; and (ii) either the retention structure or the retention element or both are offset to one another upon expansion of the stent or at least in the expanded state of the stent so that the retention element is no longer located in the retention area of the retention structure.

2. The application system of claim 1, wherein the catheter is a balloon catheter.

3. The application system of claim 2, wherein the retention structure is a band which is connected at each of the two ends of the band by a connection point to the catheter.

4. The application system of claim 1, wherein the retention structure is a band which is connected at each of the two ends of the band by a connection point to the catheter.

5. The application system of claim 4, wherein the band comprises a thermoplastic elastomer.

6. The application system of claim 5, wherein the band and the material of the catheter in the area of the connection point comprise the same material.

7. The application system of claim 4, wherein the band and the material of the catheter in the area of the connection point comprise the same material.

8. The application system of claim 1, wherein the stent has a strut which has at least one section having a zigzag or wavy shape in the crimped state, the section is used as a retention element, and the section is offset in relation to the retention structure of the catheter upon expansion of the stent.

9. The application system of claim 8, wherein the section which is used as a retention element is part of an annular peripheral strut of the stent.

10. The application system of claim 9, wherein the annular peripheral strut is situated on the stent end of the stent.

11. The application system of claim 1, wherein each retention element comprises a first arcuate section and second arcuate section, an opposing portion of each arcuate section being proximate to each other when in a non-expanded state of the stent such that any gap between the opposing portions of the first and section arcuate sections is less than the width of the retention structure and the first and second arcuate sections engage the retention structure.

12. The application system of claim 11, wherein the retention element further comprises a third arcuate section adapted for engaging the retention structure.

13. The application system of claim 12, wherein the retention structure spans at least a portion of the first, second and third arcuate sections of the retention element.

14. The application system of claim 1, wherein when the stent is in an expanded state, either a portion of the retention element stretches or at least one of the first, second and third arcuate sections move in relation to the retention structure, such that the first, second and third arcuate sections disengage from the retention structure, and wherein the stent is no longer fixed via the retention structure and the retention element.

15. The application system of claim 1, wherein each retention element contacts and engages a portion of the retention structure at both the first and second side edges.

16. The application system of claim 1, wherein the retention area is further defined by a third point of contact on the top surface of the retention structure and at least one retention element further comprises a generally straight portion which connects at least two contact points and which contacts the retention area third point of contact.

17. A catheter suitable for an application system, comprising:

a) a catheter having at least one retention structure distinct from the catheter, the retention structure comprising a band having a top surface, a bottom surface, a first end and a second end, the first and second ends being fixedly attached to the catheter; and b) a stent drawn onto the catheter using at least one retention element, the retention element having an elongated portion having generally parallel opposing sides, wherein the each retention structure provides a retention area defined by at least two distinct and opposing points of contact with the retention element and which receives and fixes the retention element, and the retention element of the stent and the retention structure of the catheter have their geometry and position tailored to one another so that:

(i) the at least one retention element is located in the retention area of the retention structure in the non-expanded state of the stent so that at least two points of contact are on the bottom surface of the retention structure; and (ii) the retention structure and/or the retention element are offset to one another upon expansion of the stent or at least in the expanded state of the stent so that the retention element is no longer located in the retention area of the retention structure and so that at least two points of contact.

18. The catheter of claim 17, wherein the retention area is further defined by a third point of contact on the top surface of the retention structure and at least one retention element further comprises a generally straight portion which connects at least two contact points and which contacts the retention area third point of contact.

19. A stent application system, comprising:

a) a catheter having (i) an exterior surface, (ii) at least one retention structure connected to the exterior surface, the retention structure having elongated portions having generally parallel opposing sides, each structure having a first side edge section and an opposing second side edge section, the sections defining at least two distinct generally coplanar and opposing points of contact, and b) a stent having an expanded state and a non-expanded state and comprising at least one retention element, the retention element having arcuate or curved sections which (i) matably receives and engages the first and second side edges section when the stent in a non-expanded state is drawn at least partially over the catheter and (ii) releases the at least one retention structure when the stent is in an expanded state.

20. An application system for a stent, comprising:

a) a catheter;

b) at least one elongated retention member connected to the catheter, the retention member having an elongated portion having generally parallel opposing first and second sides and first and second side edges and having connections to the catheter;

c) a stent adapted to fit onto the catheter; and, d) at least one retention element which is removably associated with the at least one retention member and which is adapted to removably maintain the stent on the catheter, each retention element comprising (i) a first arcuate section, (ii) a second arcuate section, and (iii) a third arcuate section, wherein an opposing portion of each of the first and second arcuate sections are disposed proximate to and generally coplanar with each other when in a non-expanded state of the stent such that any gap between the opposing portions of the first and section arcuate sections is less than the width of the retention member and the first and second arcuate sections engage the retention member, wherein each retention member provides a retention area defined by at least two distinct and opposing points of contact with the first and second side edges of the retention element and between the connections to the catheter and which receives and fixes the retention element, and the retention element of the stent and the retention member of the catheter, wherein when the stent is in a non-expanded state, the retention member spans at least a portion of the first, second and third arcuate sections of the retention element, and wherein when the stent is in an expanded state, either a portion of the retention element stretches or at least one of the first, second and third arcuate sections move in relation to the retention member such that the first, second and third arcuate sections disengage from the retention member, thereby permitting the stent to move relative to and become dissociated from the catheter.

* * * * *